United States Patent [19]
Horzewski et al.

[11] Patent Number: 5,730,741
[45] Date of Patent: Mar. 24, 1998

[54] GUIDED SPIRAL CATHETER

[75] Inventors: Michael Horzewski, Santa Clara; Jeffrey Giba, Sunnyvale, both of Calif.

[73] Assignee: Eclipse Surgical Technologies, Inc., Sunnyvale, Calif.

[21] Appl. No.: 796,636

[22] Filed: Feb. 7, 1997

[51] Int. Cl.$^6$ ............ A61B 17/00; A61B 5/00; A61M 25/01

[52] U.S. Cl. ............ 606/1; 600/585; 604/281; 606/15

[58] Field of Search ............ 128/660.03, 772; 604/96–101, 281; 606/7, 9, 11–15; 600/585

[56] References Cited

U.S. PATENT DOCUMENTS

| | | |
|---|---|---|
| 4,669,465 | 6/1987 | Moore et al. . |
| 4,846,171 | 7/1989 | Kauphausman et al. . |
| 4,917,102 | 4/1990 | Miller et al. ............ 128/772 |
| 5,054,501 | 10/1991 | Chattani et al. ............ 600/585 |
| 5,345,940 | 9/1994 | Seword et al. ............ 128/660.3 X |
| 5,542,434 | 8/1996 | Imran et al. ............ 128/772 |
| 5,632,734 | 5/1997 | Golel et al. ............ 128/772 X |
| 5,656,028 | 8/1997 | Swartz et al. ............ 604/281 X |

FOREIGN PATENT DOCUMENTS

| | | |
|---|---|---|
| 0 515 867 A2 | 12/1992 | European Pat. Off. . |
| WO 6/35469 A1 | 11/1996 | WIPO . |

*Primary Examiner*—Francis Jaworski
*Attorney, Agent, or Firm*—Ray K. Shahani; Janet Kaiser Castaneda

[57] ABSTRACT

A spiral catheter apparatus and method of use for access to, and laser or other treatment within, cavities and organs in the human body, the apparatus having a spiral member with a selected curvilinear shape, but flexible enough to assume a temporarily elongated shape such that the spiral member can be extended through the vasculature in the temporarily elongated shape and will assume the selected curvilinear shape when extended into a body cavity or organ, the spiral member formed of a superelastic or other material, the selected curvilinear shape serving to securely position the spiral member adjacent a selected surface within the body cavity or organ for laser or other treatment with a laser delivery device or other functional device on a selected surface, the apparatus further having a main catheter shaft with at least two hollow lumens extending therethrough, the first lumen for slidably guiding the main catheter shaft over the spiral member into a first position adjacent the selected surface, and the second lumen having a guide hole adjacent the distal end of the main catheter shaft for advancing a laser delivery device or other functional device through the guide hole for laser or other treatment on the selected surface within the body cavity or organ.

22 Claims, 6 Drawing Sheets

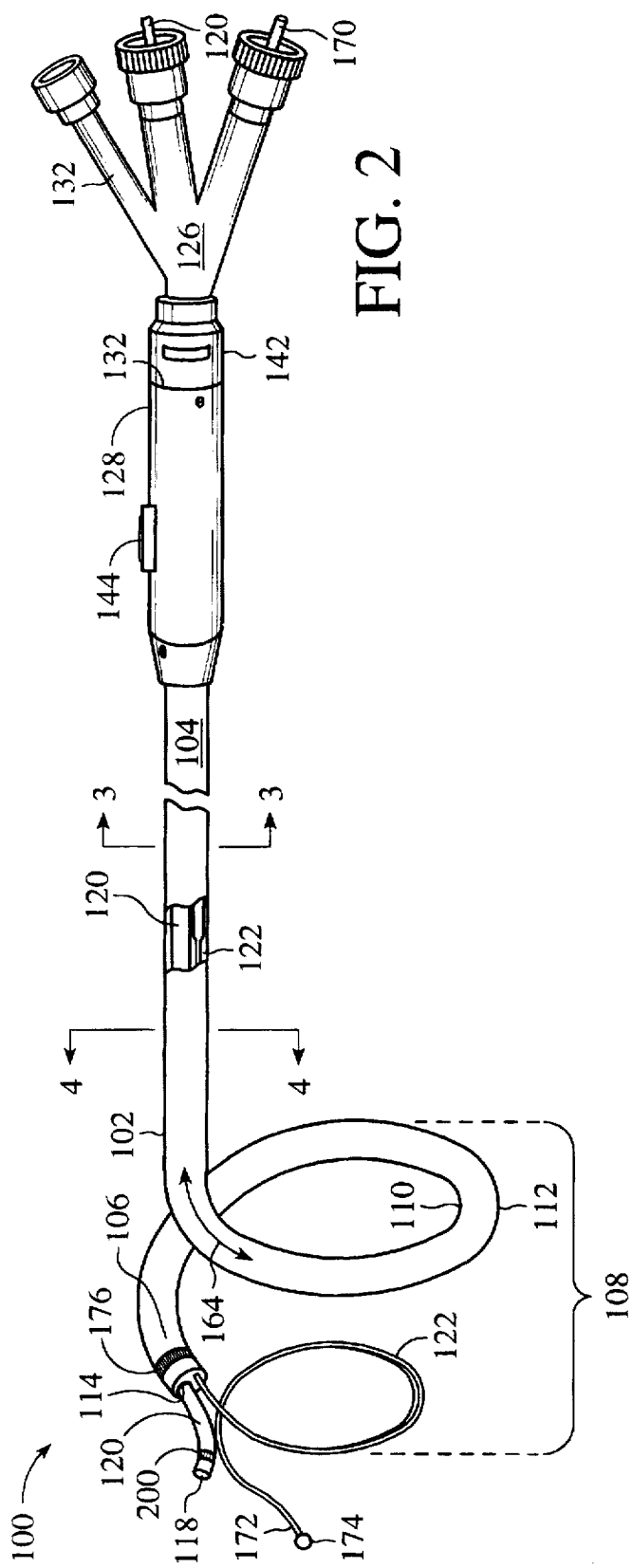
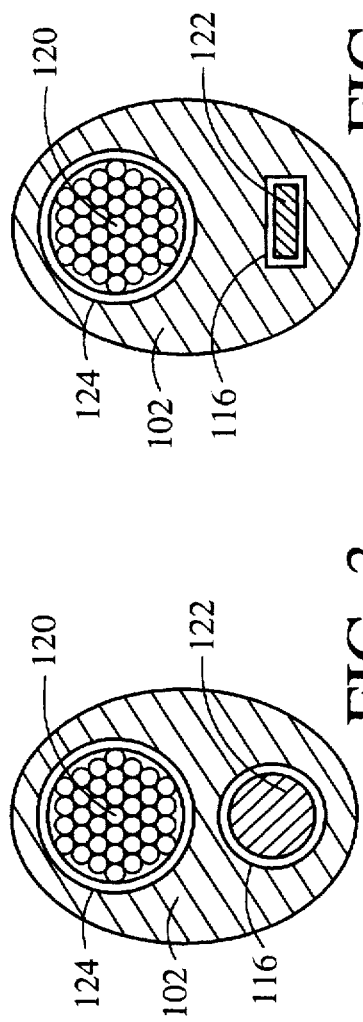

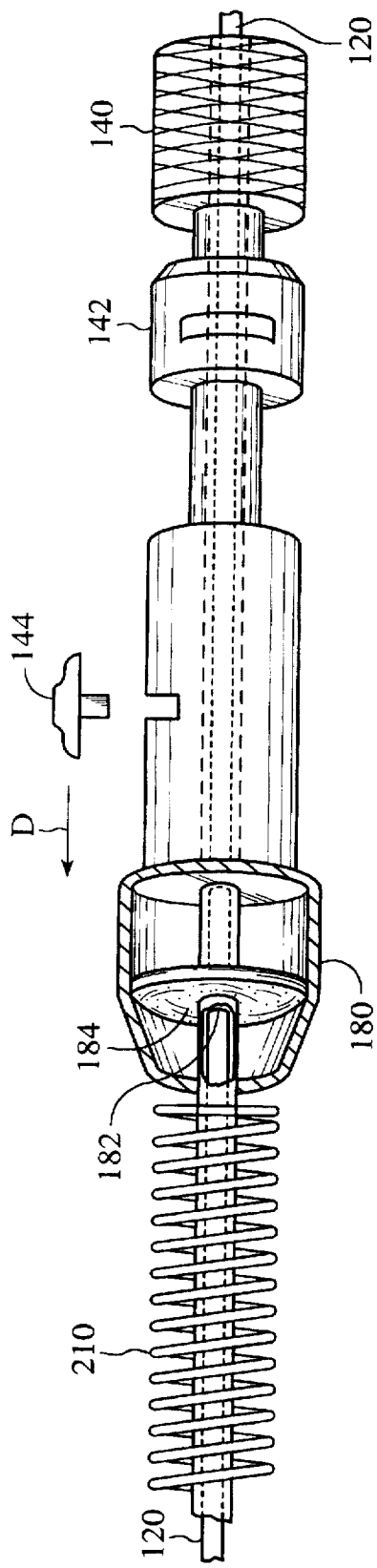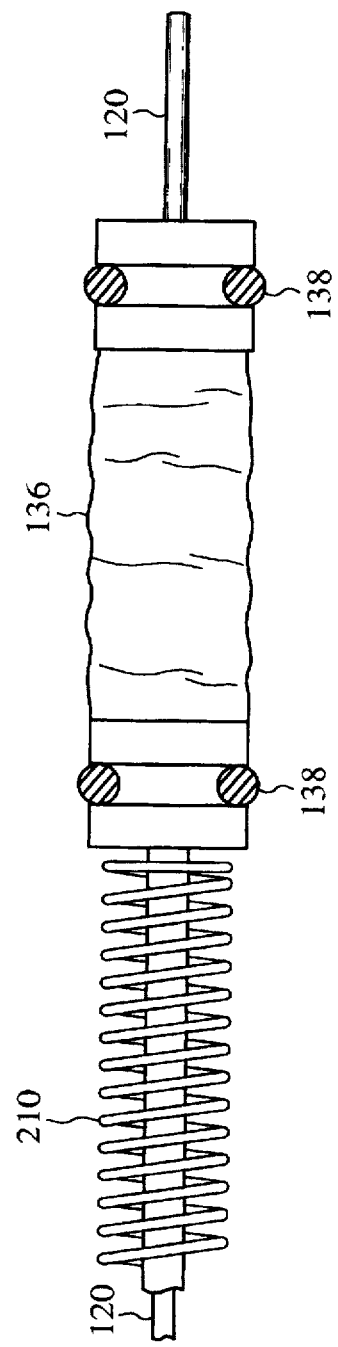
FIG. 7
FIG. 8

GUIDED SPIRAL CATHETER

RELATED APPLICATIONS

This application is related to U.S. patent application Ser. No. 08/797,240 filed concurrently herewith.

FIELD OF THE INVENTION

The present invention relates generally to catheters and catheter procedures involving laser energy delivery using fiber optic and other laser delivery systems. More particularly, the invention relates to a guided spiral catheter apparatus having a tubular catheter shaft with at least two hollow lumen regions extending therethrough, one for sliding the tubular catheter shaft over a preshaped spiral member placed within a heart chamber, organ aperture or other body opening, and the second for guiding a laser delivery means or other functional device extended therethrough, particularly adapted for use in laser-assisted transmyocardial revascularization (TMR).

BACKGROUND OF THE INVENTION

In the treatment of heart disease, one method of improving myocardial blood supply is called *transmyocardial revascularization* (TMR), the creation of channels in the myocardium of the heart. The procedure using needles in a form of surgical "myocardial acupuncture" has been used clinically since the 1960s. Deckelbaum. L. I., Cardiovascular Applications of Laser Technology, *Lasers in Surgery and Medicine* 15:315–341 (1994). The technique relieves ischemia by allowing blood to pass from the ventricle through the channels either directly into other vessels communicating with the channels or into myocardial sinusoids which connect to the myocardial microcirculation.

In the reptilian heart, perfusion occurs via communicating channels between the left ventricle and the coronary arteries. Frazier, O. H., Myocardial Revascularization with Laser - Preliminary Findings, *Circulation*, 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and resists occlusion. A thin zone of charting occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described in the prior art. U.S. Pat. No. 4,658,817 issued Apr. 21, 1987 to Hardy teaches a method and apparatus for surgical TMR using a $CO_2$ laser connected to an articulated arm having a handpiece attached thereto. The handpiece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

The foregoing discussion relates to surgical procedures, i.e. procedures which access the heart surgically, either via open heart surgery, or perhaps by minimally invasive surgical (MIS) methods if the design and size of the distal ends of the hand pieces are suitable for use in an MIS site. However, since TMR most often involves creating channels through the endocardium into the lower left chamber of the heart, it is desirable to create TMR channels in a percutaneous procedure, i.e. by extending a catheter apparatus through the vasculature into the ventricle and creating the channels through endocardial surfaces and into myocardium. Performing such percutaneous TMR is desirable for a number of reasons. Percutaneous catheter procedures are typically less traumatic to the patient compared to surgical procedures. Adhesions between the pericardial sac and epicardium are eliminated. Percutaneous TMR with a catheter apparatus also offers an alternative solution to persons who are not candidates for surgical procedures.

Because TMR procedures generally involve creating a plurality of channels within the myocardium, performing the procedure percutaneously requires the ability to steer a catheter apparatus through the vasculature and maneuver the apparatus within the ventricle of the beating heart as rapidly as possible to create the channels without subjecting the heart to the undue stress of a lengthy procedure. Additionally, the ability to control and stabilize the catheter apparatus against the beating heart wall while creating channels with a laser is desirable for percutaneous procedures to ensure creation of channels as desired and to ensure that the laser is fired only within the myocardial tissue. TMR channels should be spaced and grouped appropriately to achieve the desired result without weakening or rupturing the heart muscle.

The early myocardial acupuncture procedures were not performed percutaneously. The Hardy $CO_2$ laser delivery system described above is rigid, relatively large, and not adaptable for percutaneous use. The Aita '316 patent does not suggest a method for percutaneous use of the single aperture, laser delivery device described therein for surgical use.

U.S. Pat. No. 5,389,096 issued Feb. 14, 1995 to Aita et al. purports to teach one method of percutaneous TMR using an elongated flexible lasing apparatus with control lines and a focusing lens structure at the distal tip. The method describes the use of pressure to attempt to stabilize the apparatus against the wall of the heart. The '096 apparatus requires movement and restabilization of the apparatus prior to the creation of each channel. Neither of these patents, nor any other prior art, describes or suggests creation of more than one TMR channels without the necessity for repositioning the entire catheter device.

Several prior art patents describe the use of catheters within the ventricle for percutaneous treatment of ventricular tachycardia. Such devices have a means to locate an arrhythmia site and ablate the site, at or just below the ventricle surface, using an electrode device or laser energy. U.S. Pat. No. 5,104,393 issued Apr. 14, 1992 to Isner teaches a catheter apparatus having a guiding Y-shaped sheath and guide catheter assembly for introducing an optical fiber into the ventricle. Positioning is described to enable a single burst of laser energy from a single aperture to ablate the site. However, positioning or specific steering means sufficient to create one or more TMR channels is not described or suggested.

U.S. Pat. Nos. 5,255,679 issued Oct. 26, 1993 and 5,465, 717 issued Nov. 14, 1995 to, respectively, Imran and Imran et al., disclose non-laser, basket-shaped catheter apparatus for mapping and/or ablation of arrhythmia sites within the ventricle. A pull wire is used to expand the basket portion within the ventricle, and a plurality of electrodes on the arms of the basket are used for ablation. The basket device is designed to place the electrodes on the ventricle wall. Although the device allows for a fairly extensive mapping procedure without repositioning, no positioning means is provided for a laser delivery system to allow creation of TMR channels.

The use of superelastic and/or shape memory materials is widely known. *Structure and Properties of Ti-NI Alloys: Nitinol Devices& Components*, Duerig et al., In Press, Titanium Handbook, ASM (1994) In general, binary compositions of Nickel (Ni) and Titanium (Ti), yield alloys with shape memory and superelastic properties. These alloys are commonly referred to as Ni-Ti, nitinol, and other industry names. Their precise physical and other properties of interest are extremely sensitive to the precise Ni/Ti ratio used. Generally, alloys with 49.0 to 50.7 atomic % of Ti are commercially available, with superelastic alloys in the range of 49.0 to 49.4%, and shape memory alloys in the range of 49.7 to 50.7%. Due to a rapid decrease in the ductility of the material, binary alloys with less than 49.4 at % Ti are generally unstable. In general, these types of materials exhibit hysteresis, defined as a phenomenon exhibited by a system whose state depends on its previous history, and illustrated diagrammatically by the familiar upper and lower curves which meet at the ends and define an area under the curves. In the case of solid materials undergoing elastic hysteresis (as opposed to magnetic or electrical hysteresis), the curves are related to stress necessary to cause deformation or otherwise overcome existing stress in pre-stressed materials.

All properties of these materials change significantly as their respective "phase transformation temperatures" are approached. In general, at lower temperatures, these alloys will exist in a martensite state characterized as hard and easily deformed. However, in austenito, the high temperature phase, the alloys have a much higher yield and flow stresses. The addition of small amounts of third elements in the alloy can also have very significant effects on performance of the materials. Elements including but not limited to oxygen (O), nitrogen (N), iron (Fe), aluminum (Al), chromium (Cr), cobalt (Co) vanadium (V), zirconium (Zr) and copper (Cu), though having various effects on the Ni-Ti matrix, can have the tendency to increase strength, increase stiffess, control hysteresis and/or decrease or increase phase transition temperatures.

Ni-Ti products are commonly used in the form of cold drawn wire or as barstock. Tubing is also available. The toxicity of the alloy or the solubility or other compatibility with the biological environment in which catheter equipment is used is an important consideration. The alloys are commonly used in a cold worked and partially annealed condition. The partial anneal does not recrystallize the material but does bring about the onset of recovery processes. The extent of the post-cold worked recovery depends upon many aspects of the application, such as the desired stiffess, fatigue life, ductility, recovery stress, etc. Ni-Ti is difficult to join since most mating materials cannot tolerate the large strains experienced by Ni-Ti. Most connections will rely on crimped bonds. Although Ni-Ti can be brazed or welded to itself with relative ease, such as by resistance and with TIG methods, brazing or welding to other materials is difficult though proprietary methods do exist and are practiced in large volumes, for example in the production of eyeglass frames.

For the purposes of this disclosure, a distinction between superelastic materials and shape memory materials is made. Superelasticity, refers to the highly exaggerated elasticity, or springback, observed in many Ni-Ti alloys preformed at a specific temperature. The function of the material in many of such cases is to store mechanical energy. Though limited to a rather small temperature range, these alloys can deliver over 15 times the elastic motion of a spring steel, i.e., withstand a force up to 15 times greater without permanent deformation. Shape memory materials will refer to those materials which can be deformed, but which will freely recover their original shapes during heating, often utilizing electrical resistivity, or which will develop a large recovery stress when recovery is prevented. Applications of these shape materials include various types of fasteners and tube/pipe connectors. It will be understood that a significant difference or distinction between such superelastic and shape memory materials is the phase or transition temperature below which they may be deformable and above which they will return to their original, preferreed shape. With regard to the present invention, it will be understood that the transition temperature of materials must, in general, be somewhat above body temperature by at least 10°–12° C.

U.S. Pat. No. 3,890,977 issued Jun. 24, 1975 to Wilson teaches kinetic memory electrodes, catheters and cannulae. These devices incorporate a material, such as a Ni-Ti alloy, having heat-activated mechanical memory properties. The device is formed into an operative shape at a high temperature. Then, at a low temperature below its transitional temperature, it is reformed into a shape for ease of insertion into a guide catheter or the like or otherwise through a portion of a patient's vasculature or other body lumen. When located in the organ or other desired region, those portions of the device constructed using such shape memory materials are heated to above their transitional temperatures, using electrically resistive elements, thereby returning the catheter to its original annealed anchoring or proper locating shape. An important drawback of the Wilson apparatus is that heat must be applied to the catheter tip. Complicated construction and electrical power distribution must be considered.

As can be seen from a description of the prior art above, percutaneous TMR catheters are virtually unknown with the exception of the catheter briefly described in the '096 Aita patent. There is a need in the art for a percutaneous TMR catheter shaped to correspond to the contours of the ventricle, having means for easily positioning and repositioning the catheter to the ventricle wall, and having a port for a laser delivery means to enable rapid creation of a plurality of appropriately grouped and spaced TMR channels.

ADVANTAGES AND SUMMARY OF THE INVENTION

Thus, it is an advantage of the present invention to provide a catheter apparatus and method of use for percutaneous and other intra-vascular procedures, including TMR, or any stimulation procedure, which overcomes the limitations of the prior art.

It is a further advantage of the present invention to provide a catheter apparatus capable of being guided into a heart chamber and used therein for creating a plurality of TMR channels controllably and efficiently.

It is a further advantage of the present invention to provide a catheter apparatus made, at least in part, of a superelastic material or a shape memory material having a preformed operative shape, which, to facilitate insertion into the patent and through or into at least a portion of the vasculature or other body lumen or opening, can be temporarily deformed or straightened, such that upon positioning adjacent a selected surface, the catheter will be allowed to return or can be returned to the preformed operative shape.

It is a further advantage of the present invention to provide a catheter apparatus having at least two hollow lumens extending therethrough or partially therethrough, one for sliding the tubular catheter shaft over a preshaped spiral member placed within a heart chamber, organ aperture or other body opening, and the second for guiding a laser delivery means or other functional device extended therethrough, particularly adapted for use in laser-assisted transmyocardial revascularization (TMR).

It is yet a further advantage of the present invention to provide a percutaneous catheter which can be positioned securely into a selected position within the left ventricle.

A further advantage of the present invention is to provide an apparatus to enable creation of a plurality of appropriately grouped and spaced TMR channels on a selected surface within a body cavity or organ quickly and safely, without the need for repositioning the catheter before creation of each successive hole.

Therefore, to summarize the present invention, a guided spiral catheter apparatus having at least two hollow lumens extending therethrough or partially therethrough, one for sliding the tubular catheter shaft over a preshaped spiral member placed within a heart chamber, organ aperture or other body opening, and the second for guiding a laser delivery means or other functional device extended therethrough, particularly adapted for use in laser-assisted percutaneous transmyocardial revascularization (TMR), is disclosed herein. The preshaped spiral member, made at least partially of superelastic and/or shape memory materials of construction, has a certain, deformable, essentially spiral shape. The main catheter shaft slides over the preshaped spiral member through one of the lumens.

The preshaped spiral member is designed to be placed adjacent selected portions of tissue, such as within the left ventricle, and is somewhat flexible. Thus, a laser delivery means such as an optical fiber or fiber bundle, or other functional device, can be extended through the second lumen of the catheter shaft such that the distal tip of the laser delivery means or other functional device extends through the distal end of the second lumen at the distal end of the catheter shaft. The flexible, preshaped spiral curvature of the spiral portion of the spiral member will keep the catheter shaft in contact with the selected surface structure for treatment thereon. Thus, with regard to TMR, a laser delivery means, such as an optical fiber or fiber bundle, can be advanced through the catheter shaft for creating a series of TMR channels. Furthermore, with regard to non-laser TMR, a cannula or trocar assembly may be extended into the tissue of the left ventricle, with or without use of a mechanical piercing tool.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 2 is a representative isometric view of a preferred embodiment of the spiral catheter of the present invention.

FIG. 3 is a representative section view of a preferred embodiment of the spiral catheter of the present invention taken at 3—3.

FIG. 4 is a representative section view of a preferred embodiment of the spiral catheter of the present invention taken at 4—4.

FIG. 7 is a representative view showing the internal assembly of a preferred embodiment of a handle means of a spiral catheter of the present invention.

FIG. 8 is a representative detail view of another preferred embodiment of a blood seal internal to handle of the present invention.

DETAILED DESCRIPTION OF THE PREFERRED EMBODIMENT

Preferred Apparatus

Figure 1:
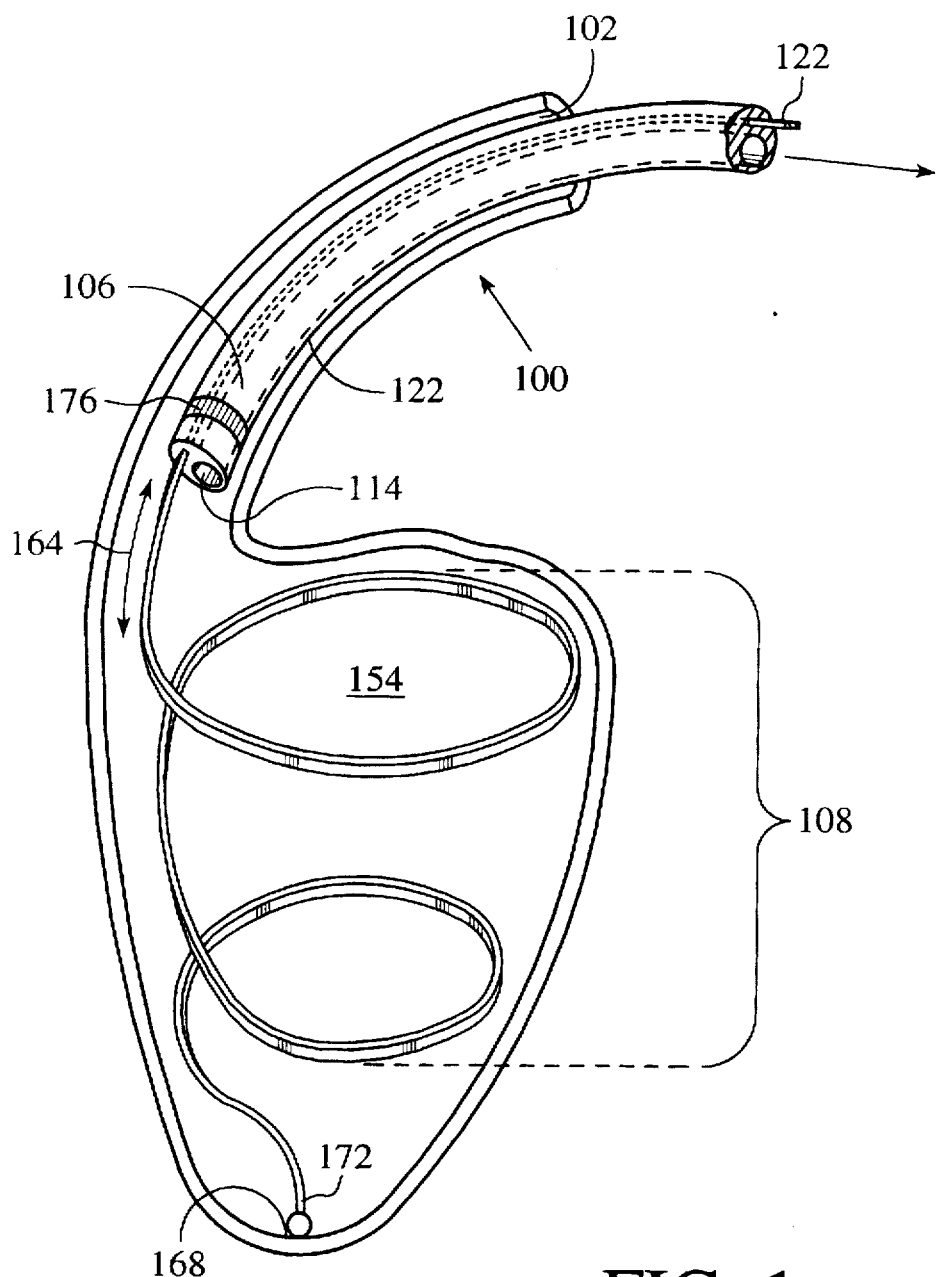
FIG. 1 is a representative view of the preshaped spiral member of the spiral catheter of the present invention within the left ventricle or other body opening.

FIG. 1 is a representative view of the preshaped spiral member 122 of the spiral catheter 100 of the present invention within the left ventricle 154 or other body opening. The preshaped spiral member 122 has a spiral portion 108, a proximal end 170 and a distal end 172. In a preferred embodiment, the spiral portion 108 can be made smaller, larger, or given a slightly different shape or configuration, depending upon the application or size of orifice to be treated. In a preferred embodiment, as shown, the spiral member 122 is positioned inside the left ventricle 154 of the heart.

FIG. 2 is a representative isometric view era preferred embodiment of the spiral catheter 100 of the present invention. A main catheter shaft 102 has both a proximal end 104 and a distal end 106. A spiral portion 108 near the distal end 106 defines an inner arcuate sidewall 110 and an outer arcuate sidewall 112. The main catheter shaft 102 has at least a first lumen 116 and a second lumen 124, as shown in FIG. 3, both extending therethrough. The main catheter shaft 102 slides over a preshaped spiral member 122 which extends slidably through the first lumen 116. The distal end 172 of the spiral member 122 extends beyond the distal end 106 of the main catheter shaft 102. A laser delivery means 120 or other functional device can extend through the second lumen 124. The distal end 118 of the laser delivery means 120 can be advanced out of the end of the second lumen 124.

A wye or other multifurcated coupling means 126 provides a manifold for individually controlling both the proximal end 170 of spiral member 122 as well as the proximal end of laser delivery means 120 or other functional device, including equipment such as tools or probes for visualization or other recording or monitoring functions, flushing or cleaning, or addition of drugs or other materials through the spiral catheter 100. Optionally, a handle means 128 can be provided at the proximal end 104 of shaft 102. Thus, an optical fiber, bundle or other laser delivery means 120 can be controllably advanced and retracted through the second lumen 124 by manipulating the handle means 128.

The preformed spiral member 122 is preferably made at least partially of, or otherwise comprises, a superelastic material which can be given a selected shape. Other suitable materials include spring steel, stainless steel, shape memory or superelastic/shape memory alloys. Once the superelastic material has been shaped, it can be said to have a memory for the shape. Upon deformation of the shaped material at temperatures somewhat below the transition temperature, the material will tend to return to the preformed shape with spring-like action. Thus, the preformed spiral member 122 can be temporarily deformed (substantially straightened) and positioned inside the left ventricle 154 or other body opening by passing it through a guide catheter 150 (see FIG. 9) through the vasculature in an essentially elongated shape. The main catheter shaft 102 is also flexible enough to be pushed and steered through bends and turns along desired paths within the body over the spiral member 122. For example, catheterization procedures often involve introducing such equipment to the human body via the femoral artery and advancing the equipment to the desired location through the vasculature. Then, once introduced into the ventricle, other heart chamber or other opening large enough, the superelastic material in the spiral portion 108 will act like a spring and retract in length while assuming the preformed shape. Finally, the spiral portion 108 will be springy enough, if and when retracted back into the main catheter shaft 102 or another guide catheter, to be temporarily deformed again. It will be understood that the handle means 128 may act as the wye coupling means 126 adapted for allowing fluid flow through the proximal end 132 of handle means 128. In the case of shape memory materials, a "memory" or preformed shape can be given to the spiral member 122. Then, the percutaneous apparatus can be straightened temporarily and extended through the vasculature. Once the distal end 172 of the deformed spiral member 122 is in position, the preformed operative shape (such as the spiral shape) can be reproduced by any number of different ways. These include heating using electrically resistive material, electrical resistance, radio frequencies, microwaves, circulating heated fluid, etc. It will also be understood that the preformed spiral member 122 could also be a type of "hypo" tube, i.e. an additional tube inside a lumen for introduction of fluids, other tools, etc. Additionally, the spiral member 122, and/or the main catheter shaft 102, may be constructed from numerous combinations of materials.

FIG. 3 is a representative section view of a preferred embodiment of the spiral catheter of the present invention taken at 3—3. FIG. 4 is a representative section view of a preferred embodiment of the spiral catheter of the present invention taken at 4—4. As shown and described, the main catheter shaft 102 has a first lumen 116 and a second lumen 124, both extending at least partially therethrough. Spiral member 122 is slidably disposed within lumen 116 of catheter body 102. The laser delivery means 120 or other functional device is extended through the second lumen 124. As shown, however, the shape of the cross section area of the first lumen 116 adjacent the proximal end 104 of the main catheter shaft 102, as shown at 3—3, is different from shape of the cross section area of the first lumen 116 the adjacent the distal end 106, as shown at 4—4. It will be understood that while the actual shapes may vary, the function of providing the preformed spiral member 122 as well as the first lumen 116 with a corresponding variation in cross section shape throughout their respective lengths is to prevent rotation of the main catheter shaft 102 about the curvilinear spiral member 122. By providing distinctive cross section geometries, the components can be "keyed" together, as desired, to prevent undesired rotation of one or the other component, as well as to provide rotational torque and/or other control to the physician. Other methods or structure for "keying" the spiral member 122 to the first lumen 116 of the main shaft 102 will be included within the scope of the present invention.

Figure 5:
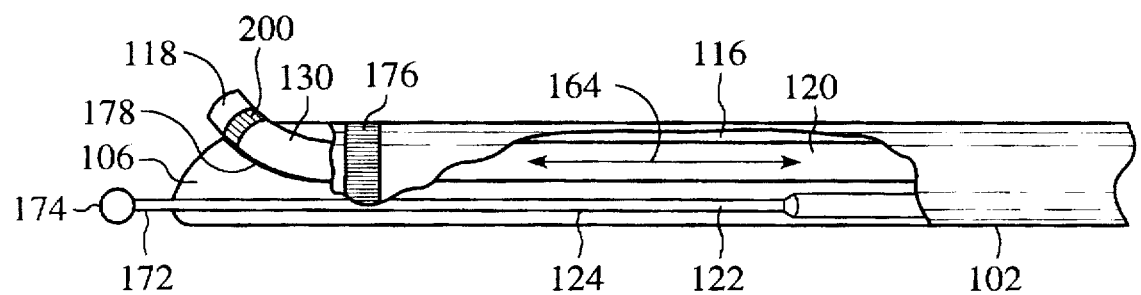
FIG. 5 is a representative section view of the distal end of a preferred embodiment of the spiral catheter of the present invention.

FIG. 5 is a representative section view of the distal end of a preferred embodiment of the spiral catheter of the present invention. In this partial view, both the distal end 172 of the spiral member 122 and the distal end 118 of the laser delivery means 120 or other functional device are shown extending outside the first lumen 116 and the second lumen 124, respectively, adjacent the distal end 106 of the catheter shaft 102. First marker 174 and second marker 176 are particularly useful in visualization via fluoroscopy or other methods. Such marker 174 and 176 can be made of platinum or other suitable radio-opaque material, and can also be placed at selected positions on the laser delivery means 120, as desired. It will also be understood that the tubing material used to build the main catheter shaft 102 can also be radio-opaque. Thus, the precise location of the distal end 106 of the catheter shaft 102 can be determined relative to the location of the distal end 172 of the spiral member 122. It will be understood that visualization enhancement aids, including but not limited to radio-opaque markers, tantalum and/or platinum bands, foils, strips or other on the various components of the present invention, including on the distal end 106 and other parts of main catheter shaft 102, on the spiral portion 108 or other parts of spiral member 122, or at any position on the laser delivery means 120, optical fiber or fiber bundle, or other functional device, will be very helpful in visualization of the percutaneous procedure. Additional radiopaque marker 200 such as a band of platinum will permit the physician to locate the distal tip 118 of laser delivery means 120 conveniently and precisely.

Figure 9:
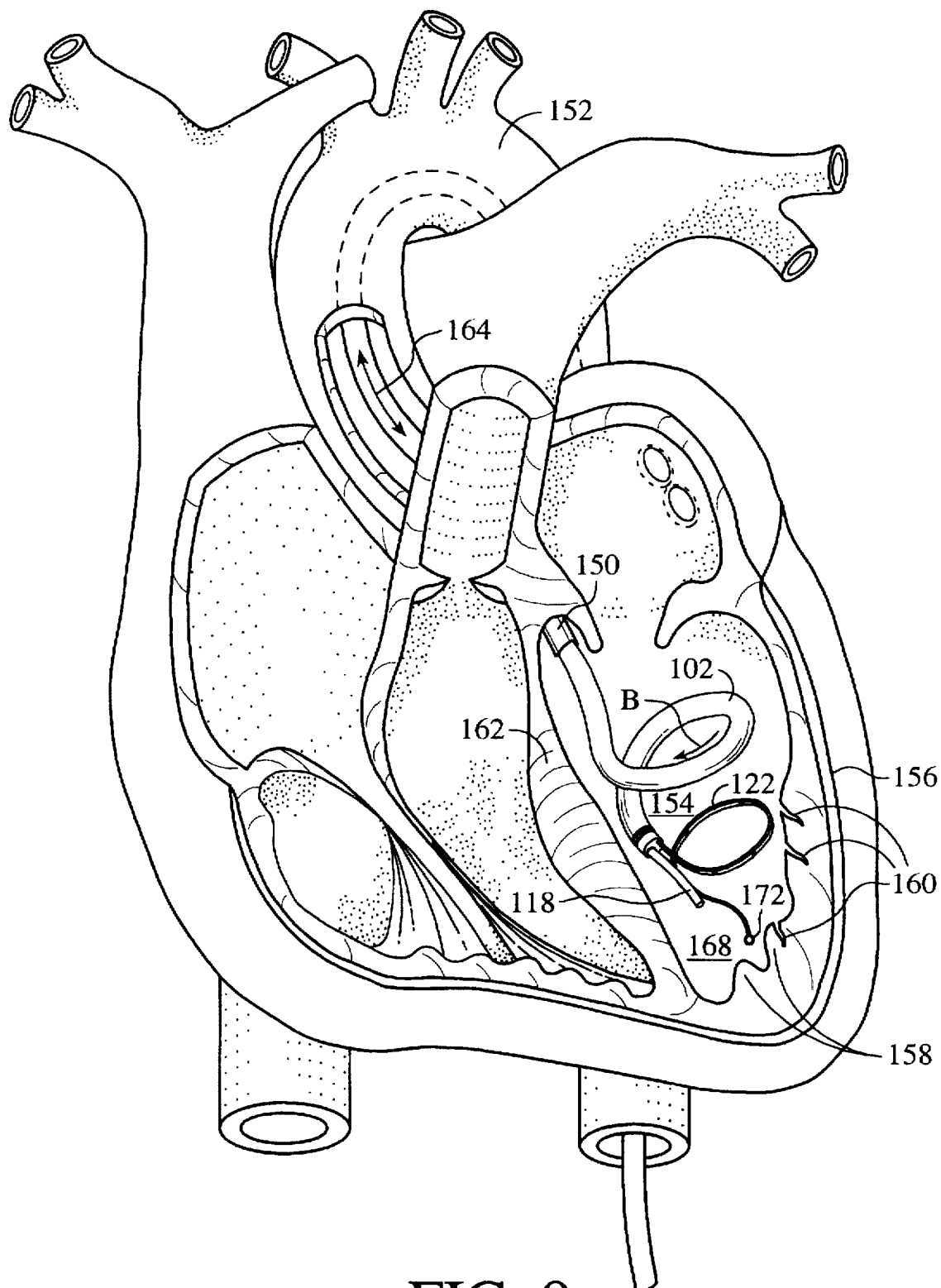
FIG. 9 is a representative perspective view of a preferred embodiment of a spiral catheter of the present invention positioned inside the left ventricle of the heart in a first position.

As best shown in FIGS. 2 and 9, the first lumen 116 lies within the inner radius of the spiral shape assumed by the catheter shaft 102 once guided over the preformed spiral member 122. Therefore, the distal end 118 of the laser delivery means 120 or other functional device advanced through the second lumen 124 will emerge out the distal end 106 of the catheter shaft 102 in a direction essentially tangential to the curvature of the spiral shape. In other words, the exit from the second lumen is operatively positioned on the main catheter shaft 102 such that the laser delivery means 120 can be advanced through the guide hole 114 at the distal end of the second lumen 124 in a selected direction, the selected direction substantially defined by the direction of the central axis 164 at a location on the spiral member 122 adjacent the distal end 106 of the main catheter shaft 102, into the selected surface 156. In the case of a preferred embodiment for TMK, a laser delivery means 120 advanced through the catheter shaft 102 will then emerge in a tangential direction relative to the spiral curvature and will be advanced through an endocardial surface at approximately the same angle to the flat surface. It will be understood that this angle will not necessarily be close to the normal wall surface.

As shown in FIG. 5, the distal end 118 of the laser delivery means 120 optionally is provided with a slight deflection or curvature 130. As will be understood, this curvature 130 will assist the physician in controllably extending and retracting the distal end 118 of the laser delivery means 120. It will be understood that the slight curvature 130 of the distal end 118 of laser delivery means 120 can be made in any of several different ways, including a permanent curvature into the cover tubing formed by heat, molding, laminated construction, etc., or a temporary curvature formed by a wire or shim construction, super elastic or shape memory material of construction, etc.

Furthermore, a cam surface 178 will optionally serve to deflect the distal end 118 of the laser delivery means 120 into an endocardial wall surface in a direction at a greater angle to the spiral shape than that formed by the tangent thereto. It will be understood that the cam surface 178 is but one possible deflection means which could be provided, other such deflection means including, and not limited to, other specifically contoured curvatures, shoulders, grooves, ramps, inserts, passages, bifurcated or multifurcated channel tips, etc. In other words, the main catheter shaft 102 optionally comprises deflection means adjacent the distal end 106 of the main catheter shaft 102 such that the laser delivery means 120 can be advanced out through the second lumen 124 in a selected direction, the selected direction substantially different than that defined by the direction of the central axis 164 at a location on the spiral member 122 adjacent the distal end 106 of the main catheter shaft 102, into the selected surface 156.

It will be understood that, as shown, the distal end 106 of the catheter shaft 102 is also very useful for a wide variety of additional/auxiliary purposes, including mounting adjunct visualization, recording or monitoring apparatus, ultrasound or electrochemical transducers thereon, etc.

Figure 6:
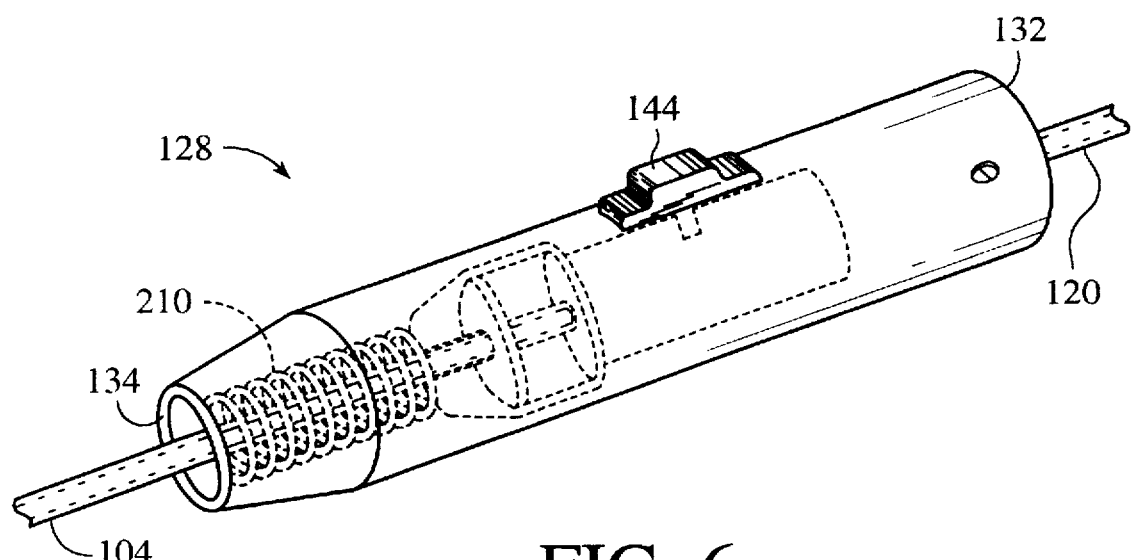
FIG. 6 is a representative isometric view of a preferred embodiment of a handle means of a spiral catheter of the present invention.

FIG. 6 is a representative isometric view of a preferred embodiment of a handle means 128 of the present invention and FIG. 7 is a representative view showing the internal assembly of a preferred embodiment of the handle means 128 of the present invention. The handle means has both a proximal end 132 and a distal end 134. Internal to handle means 128 is blood seal assembly. In the preferred embodiment, laser delivery means 120 or other functional device passes through a diaphragm member 180, consisting essentially of a small hole or aperture 182 in a flexible polymeric portion 184. Thus, a fluid seal is created by flexible portion 184 squeezed around tubular laser delivery means 120.

Adjacent the coupling means 140, depth stop bushing 142 will limit the travel of the laser delivery means 120 through the catheter assembly. Slider knob 144 mounted through slot 146 onto coupling means 140 provides a manual fiber feed mechanism. It will be understood by those skilled in the art that other laser delivery means advance mechanisms can be used with the catheter assembly 100 of the present invention. Thus, slider knob 144 mounted within slot 146 will controllably advance and retract the laser delivery means 120 through the laser delivery means or other functional device lumen 116 in the main catheter shaft 102. It will be understood, and therefore included within the scope of this invention, that the manually operated linkage laser delivery means advance mechanism can be replaced with a wide range of different mechanisms or devices, including indexed or ratcheted mechanisms, electric drives with electronic controllers, etc.

At the proximal end 132 of the handle means 128 there is a laser delivery means coupling means 140 such as a Thuoy-Borst type crimp clamp connector, etc. Other such fiber and fiber bundle coupling means 140 are included in the scope of the present invention.

FIG. 8 is a representative detail view of another preferred embodiment of a blood seal means. The apparatus comprises a collapsible piece of tubing 136 with sealing means 138 such as O-rings at either end.

It will be understood that biasing means 210 such as a coil or other type spring, as shown in FIGS. 6–8, will be placed inside handle means 128 such that the fiber advance mechanism biases the laser delivery means 120 into a fully retracted position.

FIG. 9 is a representative perspective view of a preferred embodiment of the spiral catheter of the present invention positioned inside the left ventricle 154 of the heart in a first position. As an "access-assisted system", a guide catheter 150 is introduced over the aortic arch 152 and through the aortic valve into the left ventricle 154. The use and apparatus of such guide catheters 150 is included within the scope of the present invention, although it will be apparent to those skilled in the art, based on the foregoing, that a guide catheter 150 need not be used in conjunction with a catheter apparatus of the present invention utilizing shape memory materials of construction. The spiral member 108 can be guided through the guide catheter 150 into a first position with distal end 172 seated within the apex 168 of the left ventricle 154 or other opening. The apex-seeking distal end is stabilized by the apex 168 such that during laser delivery or other treatment with laser delivery means 120 or other functional device, as well as during retraction of the laser delivery means 120, the position of the distal end 172 of spiral member 122 is maintained and TMR channels or other treatment can be performed with the laser delivery means or other functional device alternatingly extended and retracted as the main catheter shaft 102 is retracted or extended over the spiral member 122, as desired. This first position is adjacent a first selected surface 156, in this case a portion of endocardium in the left ventricle 154. In this position, the catheter can treat a series of individual preselected treatment points 158 ofendocardium. Such treatment points 158 would typically be TMR channels or stimulation sites. Following treatment, the spiral portion 108 of the apparatus 100 can be rotated in the direction shown by directional arrow B. This would result in placing the catheter 100 in another position to create additional treatment points on the selected surface 156. It will be clear that the apparatus of the present invention can be rotated about central axis 164 through a full range of angular positions so as to treat many different selected surfaces during a given procedure. As indicated above, a key feature of the present invention is the ability to stabilize the distal end 106 in the apex 168 of the left ventricle 154 to provide a stable, positioned catheter for treating at a plurality of sites conveniently and controllably. Furthermore, compressing the spiral portion 108 by continued advance of the apparatus ,will assist the physician to maintain contact between the operative, curved portion 108 and the heart wall or other surface area 156, especially in larger chambers or openings.

It will be understood that the outside diameter of the main catheter shaft 102 can, in a preferred embodiment, be made slightly larger than the valve leading into the left ventricle 154. In this embodiment, the shaft will, therefore, bear slightly against the side walls of the path through the heart and vents and, as the heart expands and contracts, will expand and contract therewith.

Figure 10:
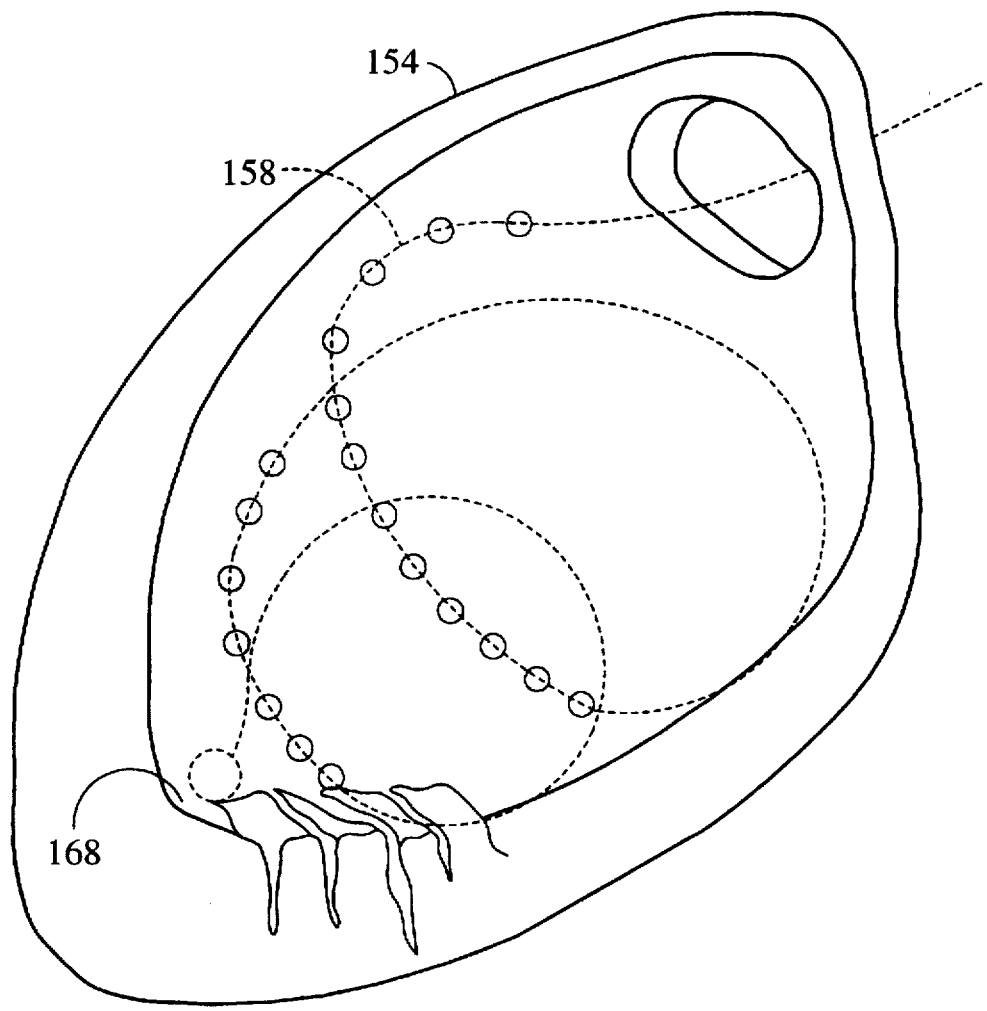
FIG. 10 is a representative top view of a treatment pattern made by a preferred embodiment of a spiral catheter of the present invention.

FIG. 10 is a representative top view of a treatment pattern made by a preferred embodiment of a spiral catheter of the present invention. This view is of the inside portion of the left ventricle 154. As described above, in the case of TMR, a first set of individual TMR channels 158 in a single spiral row or other generally spiral pattern can be created by alternatingly extending and retracting laser delivery means while repositioning the distal end of the main catheter shaft relative to spiral member. Thereafter, by precisely controlled rotation of the apparatus about its central axis 164, as shown in the prior figure, one or more additional rows or sets of individual TMR channels can be created essentially spiraling upwardly and outwardly parallel to the first set of individual TMR channels 158, to effectively cover a significant portion of interior heart wall as desired.

It will be understood that essentially any desired number or density of TMR channels can be created in a given portion of the heart. Thermal energy accumulation as well as interconnection of adjacent channels are factors, among others, to be considered in such dense TMR channeling schemes. Saline flushing and/or cooling may also be indicated in certain circumstances.

Preferred Method

As indicated above with regard to FIGS. 1–10, a preferred embodiment of the present invention is directed generally to "access-assisted systems", i.e., to catheter systems which are guided into and through parts of the body, such as into the left ventricle 154, by use of a guide catheter 150 or other guide system. Such guide catheters are well known and included within the scope of this invention. Typically, entry into the vasculature is made through the femoral artery. The physician steers the guide catheter 150 over the aortic arch 152 and across the aortic valve.

In a preferred embodiment, the preformed spiral member 122, formed of any suitable type of material having the superelastic or shape memory properties as described herein, is inserted into the guide catheter 150 and through the vasculature or other part of the body in a temporarily deformed, essentially elongated shape, and into the left ventricle 154 or other body opening. Once the spiral portion 108 of the preformed spiral member 122 is extended past the distal end 166 of guide catheter 150 inside the left ventricle, the guide catheter 150 can be retracted as desired.

Once inside the left ventricle 154, the preformed spiral member 122 will assume its operative spiral shape and be firmly positioned inside the left ventricle 154 or other body opening in a first position with the apex-seeking distal end 172 of the spiral member 122 securely stabilized and seated within the apex 168 of the left ventricle 154. Thereafter, using the spiral member 122 as a guide extending through the first lumen 116, the main catheter shaft can be extended into the ventricle 154 or other opening the distal end 106 of the catheter shaft 102 can be positioned at any position along the spiral portion 108 of the spiral member 122, including adjacent to the apex 168 of the ventricle 154 or other body opening.

At this point in the procedure, a first TMR channel 158 or other laser treated site can be created by advancing and/or retracting the distal end 118 of laser delivery means 120 to extend through the second lumen 124 and exit therefrom at the distal end 106 of the catheter shaft 102. In a preferred embodiment, this can be accomplished by manually or otherwise urging the slider knob 144 in a forward direction D toward the distal end 134 of handle means 128. As disclosed, in the case of TMR, the laser delivery means 120 could be an optical fiber or fiber bundle which would be extended into an endocardial surface 156 for the creation of channels into myocardium.

As the laser delivery means 120 is advanced, blood seal means will prevent the backflow of blood from the left ventricle 154 through shaft 102 and out the proximal end 132 of handle means 128. In a preferred embodiment, the actual length of slot 146 will determine the length of travel of the distal end 118 of laser delivery means 120 into myocardium. In the event no handle is used with the catheter assembly 100, it will be understood that any backflow preventer, check valve, blood seal, etc. with the necessary operative function and suitability can be employed at a proximal end 106 of the main shaft 102 and will be included within the scope of the present invention.

It will be understood that by providing a piercing tip or other piercing means in conjunction with the distal end 118 of laser delivery means 120, the catheter 100 can also be used initially to pierce endocardial or other selected surface 156. Such piercing or mechanical cutting device includes, but is not limited to the following: curved or flat cutting blades, hollow piercing needles, retractable, flaring, anchoring or clamping tips, and the like. The piercing tip may be any fiber bundle, or may be a sharpened fiber or fiber bundle as disclosed in U.S. patent application Ser. No. 08/638,677 filed Apr. 29, 1996, allowed incorporated herein by reference. This will minimize bleeding from the endocardium, and may also be beneficial in terms of stimulation, enhanced angiegenesis, etc. Immediately following initial piercing, advancing laser delivery means 120 a selected distance into the myocardium while simultaneously delivering laser energy will create a TMR channel or other treatment site. Alternatively, retro-lasing may be performed. This novel method includes the steps of advancing laser delivery means 120 with a piercing tip a selected distance into the myocardium and then delivering laser energy to create a TMR channel or other treatment site while simultaneously retracting the fiber, laser delivery means 120 or other functional device to create the channel as the distal end 118 of laser delivery means 120 is being retracted through myocardium. With this procedure, with regard to TMR especially, inasmuch as laser energy is only delivered during retraction of the fiber, the possibility of advancing the fiber too far and lasing through the epicardium is eliminated, the risks of complications arising from such epicardial perforations, including but not limited to cardiac tamponade (a buildup of pressure in the pericardial sac caused by the presence of an excess of fluid such as blood), proliferation of adhesions between the epicardium and the pericardial sac (thereby preventing normal, frictionless enclosure of the heart muscle within the pericardial sac), etc. are minimized.

Once a first TMR channel 158 or other laser treated site is created, slider knob 144, optionally spring loaded or otherwise automatically retracting, can be repositioned so as to retract the distal end 118 of laser delivery means 120 back through guide hole 114 and into shaft 102. Slight retraction of the catheter shaft 102 over the spiral member 122 will result in the distal end 106 of catheter shaft 102 being relocated to a different part of the spiral portion 108. Then, by advancing laser delivery means 120 back through the second lumen 124, the distal end 118 of laser delivery means 120 can be used to create additional TMR channels. As disclosed, a slight deflection or curvature 130 located at or adjacent the distal end 118 of laser delivery means 120 will assist the physician in controllably advancing the distal end 118 of laser delivery means 120 into myocardium or other body tissue to create the TMR channel or other channel extending into myocardium at a greater angle than would correspond to the natural tangential direction to the spiral member 122.

Therefore, while in a first position or orientation within the left ventricle 154, a series of TMR channels 158 will be created with the first channel made in, at or near the apex 168 of the left ventricle 154, and with successive channels created essentially and substantially in an outwardly and upwardly spiraling line ascending the endocardial surface 156 from bottom to top. Additionally, rotation of the catheter apparatus about its central axis 164 will allow the apparatus to be repositioned into a second position such that it can be placed adjacent additional surfaces or structures for treatment thereon or therein. By repeating the sequence, an entire TMR procedure placing a large number of appropriately grouped and spaced TMR channels from one or more endocardial surfaces can be accomplished rapidly and uniformly.

Furthermore, adjunct use of appropriate drug delivery apparatus, blood seal means, depth stop apparatus such as clamps, etc., visualization means, marker means as well as other hardware and methodology will be considered within the scope of the present invention. Additionally, use of electro physiology (EP) for confirming tissue contact will be particularly useful.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, mirrors configurations and other laser delivery means with and without focusing lens and the like. It will also be understood that the apparatus and method of the present invention as described herein, including the novel combination or use with any conventional mechanism or method which are known to those skilled in the art, are included within the scope of this invention. Furthermore, with regard to non-laser TMR, a cannula or trocar assembly may be extended into the tissue of the left ventricle, with or without use of a mechanical piercing tool.

It will further be understood that while the present invention has been described for performing TMR on endocardial surfaces in the left ventricle, the apparatus and methods described herein are equally intended for use in any suitable procedure, including but not limited to procedures where any device need be extended through a guide catheter to an opening or other point within the body for other medical procedures including laser treatment, visualization, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A catheter device for treating a body, the device comprising:

a treatment device;

a flexible preformed guide wire having a proximal end and a distal end, the distal end has a changeable curvilinear shape that initially has a straightened form during introduction into the body, and subsequently transforms into a conformal spiral shape within a body cavity; and a flexible catheter shaft having a proximal end and a distal end and at least two lumens extending axially therethrough, the guide wire is slidably disposed within the catheter shaft and extendable out of a first lumen a guide hole at the catheter shaft's distal end communicates with a second lumen, the treatment device is slideably disposed within the second lumen and extendable through the guide hole to selectable treatment sites such that the catheter shaft is adapted to advance along the guide wire while transformed in the conformal spiral shape, whereby the conformal spiral shape of the guide wire provides: i) a predetermined spiral treatment locus for the selectable treatment sites and ii) stabilizes the catheter device.

2. The device of claim 1 wherein the guide wire is formed at least partially from a material selected from the goup consisting of superelastic material and shape memory material.

3. The device of claim 1 further including advance means for controlling advancement of the treatment device through the second lumen.

4. The device of claim 3 further including a means for holding the catheter device's proximal end.

5. The device of claim 1 further including a depth stop means for limiting advancement of the treatment device through the second lumen.

6. The device of claim 5 further including a means for holding the catheter device's proximal end.

7. The device of claim 1 further including fluid seal means for preventing fluid flow through the catheter shaft's proximal end.

8. The device of claim 1 wherein the second lumen's guide hole is oriented in a direction substantially parallel to the guide wife's axial direction.

9. The device of claim 1 wherein the second lumen's guide hole is oriented in an offset direction to the guide wire's axial direction by a formed surface.

10. The device of claim 1 wherein the treatment device is a laser energy delivery device with a distal end having at least one optical fiber.

11. The device of claim 10 wherein the at least one optical fiber's distal end has a focusing device.

12. The device of claim 1 further including a piercing means for mechanically piercing a tissue surface.

13. The device of claim 12 wherein the piercing means is attached to the distal tip of the catheter shaft.

14. The device of claim 12 wherein the piercing means is the treatment device which is an laser energy delivery device whose optical fiber's distal end forms the piercing means.

15. The device of claim 1 further including a guide catheter disposed around the catheter device.

16. A method of positioning a catheter device in a human body for treatment at a selectable treatment site, the method comprising the steps of:

a) providing a catheter device that includes a treatment device, a flexible preformed guide wire having a proximal end and a distal end, the distal end has a changeable curvilinear shape that initially has a straightened form during introduction into the body, and subsequently transforms into a conformal spiral shape within a body cavity, and a flexible catheter shaft having a proximal end and a distal end and at least two lumens extending axially therethrough, the guide wire is slidably disposed within the catheter shaft and extendable out of a first lumen, a guide hole at the catheter shaft's distal end communicates with a second lumen, the treatment device is slideably disposed within the second lumen and extendable through the guide hole;

b) positioning the guide wire's distal portion in the body cavity so that the changeable curvilinear shape transforms into the conformal spiral shape, the guide wire's distal portion is adjacent a first spiral treatment suffaace within the body cavity;

c) moving the catheter shaft on the guide wire to a first selected site; and d) advancing the treatment device's distal end through the guide hole to the first selected site and treating the first selected site.

17. The method of claim 16 further including the following steps:

e) retracting the treatment device's distal end into the guide hole;

f) re-positioning the catheter shaft into a second spiral treatment surface within the body cavity adjacent to the first spiral treatment surface within the body cavity by moving the catheter shaft over the guide wire; and g) advancing the treatment device's distal end through the guide hole to a second selected site and treating the second selected site.

18. The method of claim 16 wherein the body surface being treated is an endocardial surface within the heart's left ventricle.

19. The method of claim 16 wherein treatment is myocardial revascularization and the treatment device is a laser energy delivery device.

20. The method of claim 16 wherein treatment is myocardial revascularization and the treatment surface is a heart's endocardial surface within a left ventricle, the method further including the step of advancing the distal end of the treatment device through the endocardial surface into the heart's myocardium while simultaneously delivering laser energy.

21. The method of claim 20 wherein the step of advancing the laser energy delivery device into myocardium while simultaneously delivering laser energy is preceded by a step of piercing the endocardial surface with the laser energy delivery device's distal end.

22. The method of claim 16 wherein treatment is myocardial revasculaxization and the treatment surface is a heart's endocardial surface within a left ventricle and the treatment device is a laser energy delivery device, the method further including the steps of advancing the distal end of the treatment device through the endocardial surface into the heart's myocardium and subsequently retracting the laser energy delivery device from the heart's myocardium while simultaneously delivering laser energy.

* * * * *